United States Patent [19]

Ohta et al.

[11] 4,413,502

[45] Nov. 8, 1983

[54] GAS DETECTING SENSOR

[75] Inventors: Minoru Ohta; Yutaka Hattori, both of Okazaki; Tomio Kawakami, Nishio; Michitoshi Onoda, Toyohashi, all of Japan

[73] Assignee: Nippon Soken, Inc., Nishio, Japan

[21] Appl. No.: 352,562

[22] Filed: Feb. 26, 1982

[30] Foreign Application Priority Data

Apr. 27, 1981 [JP] Japan .................................. 56-63625
Nov. 30, 1981 [JP] Japan ............................. 56-192476

[51] Int. Cl.$^3$ .......................................... G01N 27/12
[52] U.S. Cl. ......................................... 73/23; 338/34
[58] Field of Search ............. 73/23, 27 R; 324/71 SN; 338/34; 340/634; 422/98

[56] References Cited

U.S. PATENT DOCUMENTS

| | | | |
|---|---|---|---|
| 3,933,028 | 1/1976 | Laud et al. | 73/23 |
| 4,007,435 | 2/1977 | Tien | 73/23 |
| 4,012,709 | 3/1977 | Logothetis et al. | 73/23 |
| 4,045,764 | 8/1977 | Ichinose et al. | 338/34 |

Primary Examiner—Stephen A. Kreitman
Attorney, Agent, or Firm—Cushman, Darby & Cushman

[57] ABSTRACT

A high sensitive and high responsive gas detecting sensor for detecting the partial pressure of oxygen gas in the exhaust gases is disclosed. The sensor is provided with a sensing element having an electrical characteristic in response to the partial pressure of oxygen gas, a ceramic base member which supports the sensing element so that the sensing element is exposed to the exhaust gases, and electric current conducting means for supplying an electric current to the sensing element. The sensing element is formed of alloy ceramic material composed of 20 to 60 mol percent of cobalt monoxide, 20 to 60 mol percent of magnesium monoxide and 10 to 50 mol percent of nickel monoxide. In the preferred embodiment, the base member is formed into a plate shape and the sensing element is formed on the base member like a film.

12 Claims, 12 Drawing Figures

GAS DETECTING SENSOR

BACKGROUND OF THE INVENTION

The present invention relates to a gas detecting sensor, particularly to a sensor for detecting the partial pressure of oxygen gas contained within exhaust gases discharged from an internal combustion engine of an automobile or the like and measuring air to fuel ratio of the combustion mixture to be supplied into the internal combustion engine.

Recently, "lean burn system" that ia, the system of operating an internal combustion engine with an air to fuel ratio larger than the stoichiometric value thereof so as to reduce harmful components contained within the exhaust gases and lower the fuel consumption, has been proposed and employed practically.

The above described "lean burn system" requires a detecting means for accurately detecting air to fuel ratio in a range of lean mixtures.

U.S. Pat. Nos. 3,933,028 and 4,012,709 disclose examples of such a detecting sensor as described above.

These detecting sensors are provided with a sensing element formed of a solid solution of an alloy of cobalt monoxide(CoO) and magnesium monoxide(MgO) so as to avoid a phase change of cobalt monoxide into tricobalt tetroxide ($Co_3O_4$).

The sensing element is heated and maintained at a predetermined temperature, such as 900° C. so as to compensate output fluctuation caused by the temperature change and to prevent the above described phase change, when the detecting sensor is used.

However, the above described sensing element formed of cobalt monoxide-magnesium monoxide has such a problem that the electrical resistance of the element does not largely change in response to the change of the partial pressure of oxygen so that the correct air to fuel ratio cannot be measured.

Furthermore, in the conventional detecting sensor, the heating means has been produced by winding a linear heating member like a coil so that the structure thereof is complex and that the process of mounting the heating means to the detecting sensor is complicated.

And since the sensing element of the conventional detecting sensor has a cylindrical or disc-like shape, the thickness thereof is large so that the element does not rapidly respond to the change of the partial pressure of oxygen.

Since the heating member is provided in such a manner as to surround the sensing element without contacting therewith, it takes a while for heating the sensing element to a predetermined temperature and the consumption of electric power becomes large.

Accordingly, one object of the present invention is to provide a high sensitive sensing element of which electrical resistance largely changes in response to the change of the partial pressure of oxygen gas.

Another object of the present invention is to provide a gas detecting sensor having a simple structure, which comprises a sensing element having excellent responsive characteristic to the change of the partial pressure of oxygen gas, which does not consume large electric power for heating the sensing element and which can be easily produced.

DESCRIPTION OF THE DRAWINGS

Other objects and advantages of the invention will become apparent from the following description of embodiments thereof with reference to the accompanying drawings wherein.

SUMMARY OF THE INVENTION

The above described one object of the present invention can be attained by forming the sensing element of an alloy ceramic composed of 20 to 60 mol percent of cobalt monoxide, 20 to 60 mol percent of magnesium monoxide, and 10 to 50 mol percent of nickel monoxide.

And the above described another object of the present invention can be attained by providing a film-shaped sensing element on the surface of the heat resistant and electrically insulating base member and providing a film-shaped heating member on the surface of the base body and/or inside thereof.

DETEILED DESCRIPTION OF THE INVENTION

Hereinafter, the structure of the gas detecting sensor of the present invention will be explained in detail in accordance with embodiments with reference to the accompanying drawings as well as the producing method thereof.

Figure 1:
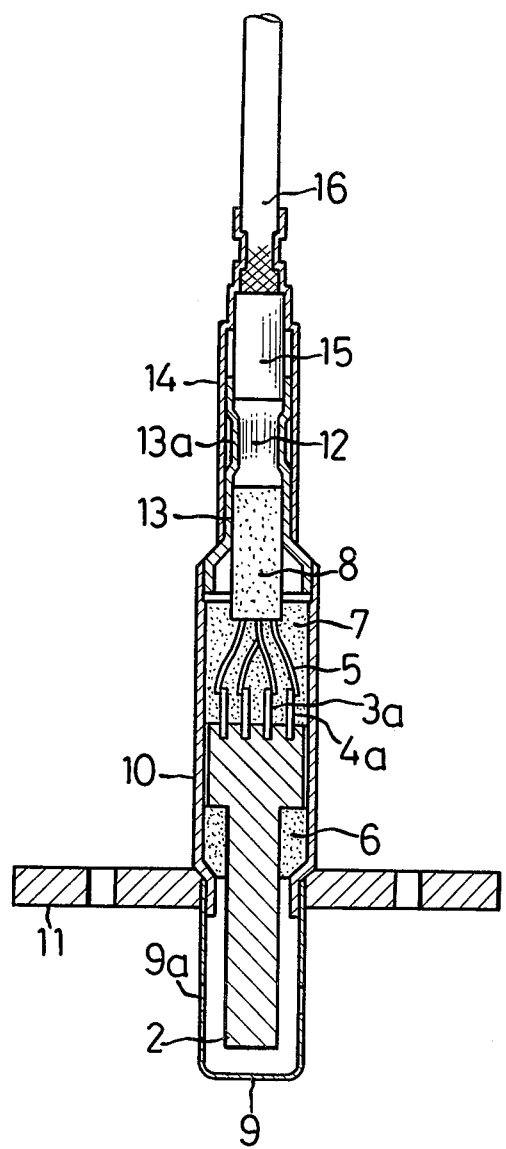
FIG. 1 is a sectional view of a gas detecting device wherein a gas detecting sensor according to the present invention is accomodated.

FIG. 1 illustrates a gas detecting device wherein a first embodiment of a gas detecting sensor according to the present invention is accomodated.

In FIG. 1, a base body 2 retains a sensing element (not shown) and electrodes (not shown) on one surface thereof, and a heater (not shown) is embedded therein.

The base body 2 is made of alumina and formed into a plate shape.

To the top end of the base body 2, lead wires 3a and 4a are fixed and each lead wire is electrically connected to the electrodes or the heater.

To each end of the lead wires 3a and 4a, sub-lead wire 5 made of heat resistant metal such as stainless steel is connected.

The base body 2 is accomodated within a protecting cover member 9 made of heat resistant metal and provided with holes 9a for introducing exhaust gases therein, and a pipe member 10 is connected to the cover member 9. In the connecting portion of the protecting cover member 9 and the pipe member 10, a flange member 11 for fixing the cover member 9 and the pipe member 10 to an exhaust pipe (not shown) is mounted.

The base body 2 is supported by a retaining member 6 made of a sintered body such as alumina within the pipe member 10. And the top portion of the base body 2, the lead wires 3a and 4a and the sub-lead wires 5 are fixed within the pipe member 10 by means of inorganic binding agent 7.

To the pipe member 10, pipe members 13 and 14 are connected in order. Within the pipe members 13 and 14, an insulating pipe 8 made of alumina or the like, a bush 12 made of fluorine-contained rubber or the like and a heat resistant rubber member 15 made of silicon rubber or the like are accomodated and the sub-lead wires 5 are inserted therethrough and extend outside the pipe member 14 with being covered by a covering member 16.

Figure 2:
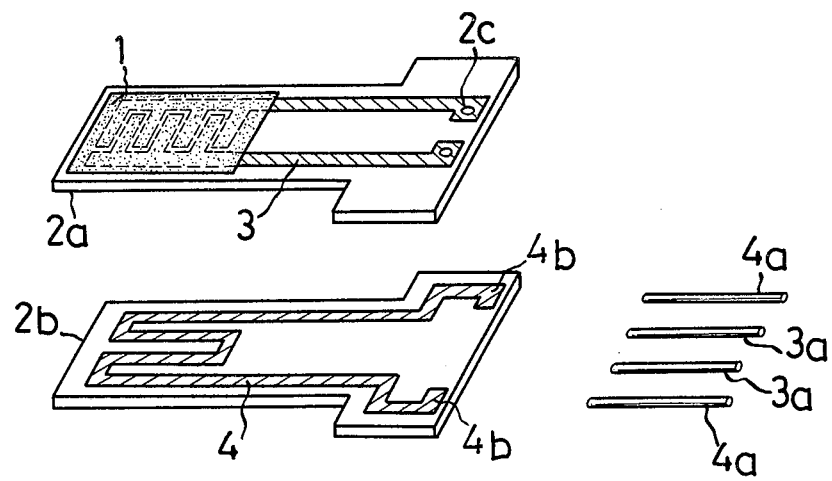
FIG. 2 is an exploded perspective view illustrating the assembling state of parts of a detecting sensor of a first embodiment according to the present invention.
Figure 3:
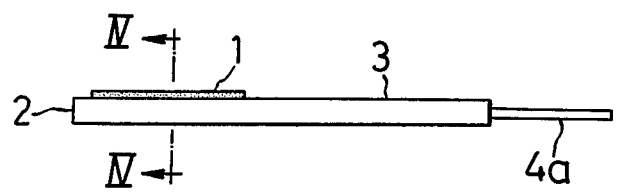
FIG. 3 is a side view of the detecting sensor of the first embodiment.
Figure 4:
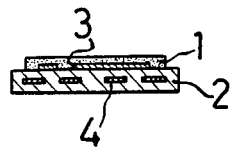
FIG. 4 is a sectional view taken along the line IV—IV of FIG. 3.

Hereinafter, the producing method of a first embodiment of the gas detecting sensor according to the present invention will be explained with reference to FIGS. 2 to 4.

At first, green sheets 2a and 2b made of alumina are prepared.

On the upper surface of one green sheet 2a, a pair of electrodes 3 are formed by screen printing method of paste like a filem.

The electrodes 3 are made of heat-resistant metal, such as platinum or platinum-rhodium alloy. One end of each electrode 3 is formed like teeth of a comb while the other end thereof extends to each of through holes 2c formed in the green sheet 2a.

And the sensing element 1 is formed by screen printing method so as to cover the teeth shaped ends of the electrodes 3. The sensing element 1 is formed of the paste composed of 20 to 60 mol % of cobalt monoxide, 20 to 60 mol % of magnesium oxide and 10 to 50 mol % of nickel monoxide.

The paste for use as the sensing element is prepared by the following method.

At first cobalt monoxide powder, magnesium monoxide powder and nickel monoxide powder are prepared, respectively.

And these powders are thoroughly mixed by wet process so as to have the above described composition ratio and fired within an electric furnace at 1300° C. for about two hours. The obtained fired body is milled and mixed. Then, the obtained mixture is refired at 1300° C. for about two hours.

These milling, mixing and firing steps are repeated until the obtained sintered body exhibits peaks of a single phase upon X-ray diffraction.

Next, the obtained sintered body is milled and mixed with ethyl cellulose as binder and terpineol as solvent by thoroughly stirring together to form paste to be printed on a base body of the gas detecting sensor.

On the upper surface of the other green sheet 2b, a heater 4 is formed like a film by screen printing method of paste.

The heater 4 is made of platinum, platinum-rhodium alloy, tungsten, or molybdenum-manganese alloy.

The green sheets 2a and 2b are combined so that the under surface of the green sheet 2a contacts with the upper surface of the green sheet 2b.

At this time, a pair of lead wires 4a are disposed between the sheets 2a and 2b so that each end thereof is contacted with each end 4b of the heater 4 and another pair of lead wires 3a are also disposed between the sheets 2a and 2b so that each end thereof is opposed to each through hole 2c of the sheet 2a.

The combined sheets 2a and 2b are pressed while being heated. Then, the pressed sheets 2a and 2b are fired at 1500° to 1600° C. within an electric furnace for about five hours. As a result, the sheets 2a and 2b are sintered together to form an integral base body provided with a film shaped heater 4 formed therewithin and a film shaped electrodes 3 formed thereon. At the same time, the lead wires 3a and 4a are firmly fixed between the sheets 2a and 2b.

Next, the paste of cobalt monoxide, magnesium monoxide, nickel monoxide is printed on the electrodes 3 by screen printing method. After being dried, the base body is fired at 900° C. within an electric furnace for about two hours to form a sensing element 1.

At this time, the through holes 2c may be coated with electric-conductive paste in order to improve the electrical connection between the lead wires 3a and the electrodes 3.

EXPERIMENT

By changing the composition ratio of cobalt monoxide, magnesium monoxide, and nickel monoxide as shown in the following table, various kinds of paste were prepared. And various kinds of sensing elements were made of various kinds of paste. In the table, Samples 1 to 10 are elements made of the paste having the composition ratios within the scope of the present invention and Samples 10 to 17 are elements shown for comparision. Sample 17 is an element having the same composition ratio as that of the conventional element.

And experiments were made on several properties of Samples 1 to 17 which were accomodated in the gas detecting device and mounted in an exhaust passage of an engine of an automobile.

The result of the experiments are also shown in the following table.

METHOD OF EVALUATION (1) Sensitivity to oxygen (n):

Generally, the electrical resistance R of such a semiconductive ceramic as the material of the sensing element according to the present invention is expressed by the formula: $R = A \times P_{O_2}^{1/n}$, where A is a constant and $P_{O_2}$ is the partial pressure of oxygen gas.

The sensitively of the sensing elements to $P_{O_2}$ depends on the value of n. Namely, as the value of n is decreased, the sensitivity of $P_{O_2}$ is increased.

The logarithms of both sides of the above formula are taken ($\log R = 1/n \log P_{O_2} + A'$) and n is obtained from the inclination of the straight line of the graph thereof.

(2) Stability:

Durability tests were made under the following two conditions. And when peaks other than those of a single phase of the first stage were observed in one sample upon the X-ray diffraction, that sample was judged inferior and X mark was inserted in the table.

(i) Oxidizing atmosphere: within an electric furnace 850° C. × 24 hours (air atmosphere)

(ii) Reducing atmosphere: within exhaust gases 850° C. × 50 hours (air/fuel ratio A/F = 12)

(3) Responsiveness:

six cylinders, 4 cycles, 2000 cc engine 2000 rpm, −250 mm Hg

The air to fuel ratio (A/F) is forcibly varied from 15 to 19 by 2.5 seconds and this cycle is repeated.

Figure 5:
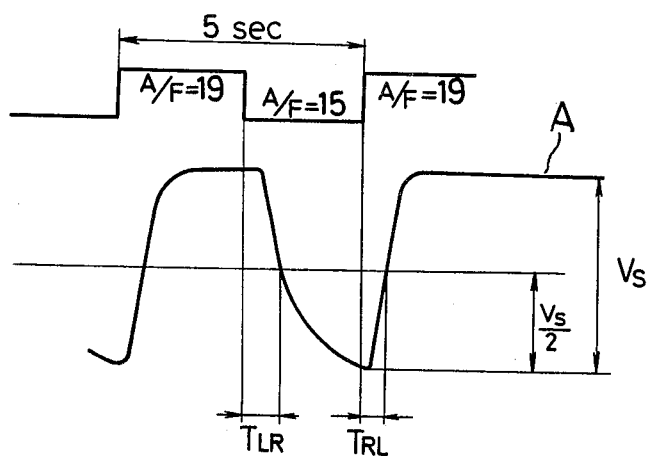
FIG. 5 is a graph illustrating responsive characteristic of the sensing element to be mounted on the detecting sensor.

In FIG. 5, the line A shows the variation of the resistance of the sensing element in response to the variation of the air to fuel ratio. Vs shows the width of the variation of the line A.

The responsiveness was evaluated by the total time of the time (TLR) between the moment when the air to fuel ratio is varied from 19 to 15 and that when the resistance is varied by Vs/2, and the time(TRL) between the moment when the air to fuel ratio is varied from 15 to 19 and that when the resistance is varied by Vs/2.

And the sensing elements of which response time is not less than 1 second were judged inferior.

(4) Electrical resistance:

When the gas detecting sensor is mounted in the internal combustion engine of an automobile or the like, the preferable electrical resistance thereof is not more than 1 M$\Omega$.

When the electrical resistance is above 1 M$\Omega$, the sensor is apt to mis-operate due to various noises such as ignition noise and electric power source noise. Therefore, the sensors of which electrical resistance is about 1 M$\Omega$ were judged inferior.

The electrical resistance was measured by using the engine of six cylinders, four cycles and 2000 cc under the driving condition: 2000 rpm, −250 mmHg, 850° C. (heating temperature of the heater) and A/F=18.

| Sample No. | CoO | MgO | NiO | Sensitivity to oxygen (n) | Stability | Response time (second) | Electrical resistance (A/F = 18) | Judgement |
|---|---|---|---|---|---|---|---|---|
| 1 | 60 | 25 | 15 | 3.5 | O | 0.55 | 95K$\Omega$ | O |
| 2 | 40 | 20 | 40 | 3.0 | O | 0.75 | 750K$\Omega$ | O |
| 3 | 30 | 30 | 40 | 2.7 | O | 0.70 | 800K$\Omega$ | O |
| 4 | 20 | 65 | 15 | 3.3 | O | 0.60 | 700K$\Omega$ | O |
| 5 | 40 | 30 | 30 | 3.1 | O | 0.70 | 210K$\Omega$ | O |
| 6 | 50 | 40 | 10 | 3.4 | O | 0.50 | 100K$\Omega$ | O |
| 7 | 25 | 40 | 35 | 3.3 | O | 0.70 | 170K$\Omega$ | O |
| 8 | 15 | 50 | 35 | 3.4 | O | 0.70 | 790K$\Omega$ | O |
| 9 | 60 | 20 | 20 | 3.3 | O | 0.65 | 72K$\Omega$ | O |
| 10 | 20 | 30 | 50 | 3.0 | O | 0.85 | 800K$\Omega$ | O |
| 11 | 25 | 20 | 55 | 2.9 | O | 1.2 | 3.2M$\Omega$ | X |
| 12 | 65 | 20 | 15 | 3.5 | X | 0.55 | 70K$\Omega$ | X |
| 13 | 70 | 20 | 10 | 3.5 | X | 0.45 | 50K$\Omega$ | X |
| 14 | 40 | 15 | 45 | 3.1 | X | 0.85 | 150K$\Omega$ | X |
| 15 | 0 | 30 | 70 | 2.9 | X | 1.6 | 7.9M$\Omega$ | X |
| 16 | 50 | 0 | 50 | 2.8 | X | 0.80 | 620K$\Omega$ | X |
| 17 | 30 | 70 | 0 | 4.2 | O | 0.50 | 450K$\Omega$ | X |

As is apparent from the table, n of the sensing element formed of cobalt monoxide, nickel monoxide, and magnesium oxide is 2.7 to 3.5. Compared with Sample 17 which is the conventional element formed of cobalt monoxide and magnesium monoxide(n=4.2), sensitivity of the sensing elements (Samples 1 to 10) of the present invention to the oxygen is remarkably improved.

However, when the amount of cobalt monoxide is above 60 mol % (Samples 12 and 13) or magnesium monoxide is below 20 mol % (Samples 14 and 16) stability of the sensing element is inferior to that of others. And when nickel monoxide is above 50 mol % (Samples 11 and 15) response time is not less than 1 second so that these samples are judged inferior.

Namely, Samples 1 to 10 of which composition ratio is within the range of 20 to 30 mol % of cobalt monoxide, 20 to 60 mol % of magnesium monoxide and 10 to 50 mol % of nickel monoxide exhibit excellent result on all of the sensitivity to oxygen(n), stability, response time and electrical resistance.

In the first embodiment of the gas detecting sensor having the above described structure, according to the present invention, the film shaped heater 4 and the film-shaped sensing element 1 are integrally formed on the base body 2 and the film-shaped heater 4 is disposed close to the sensing element 1.

When the film-shaped heater 4 is heated by applying electric current thereto, the temperature of the sensing element 1 rapidly rises. And large electric power is not consumed for heating the sensing element to a predetermined temperature.

Since the sensing element 1 is formed thin like a film, exhaust gases rapidly diffuse into the whole of the sensing element 1 so that the response time thereof is very short.

In the above described first embodiment, the sensing element is formed on the base body like a film.

Figure 6:
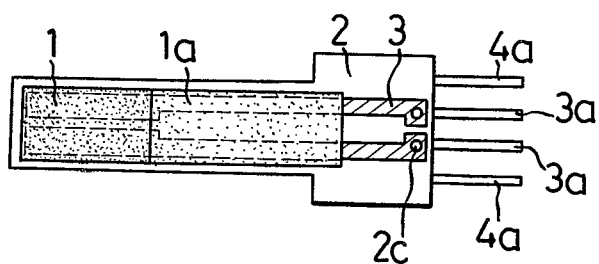
FIG. 6 is a plan view of a second embodiment of a detecting sensor according to the present invention.
Figure 7:
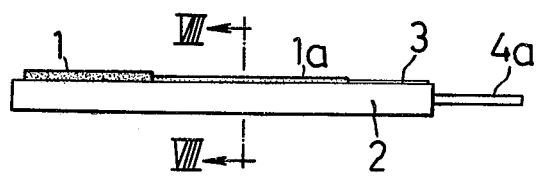
FIG. 7 is a side view of the second embodiment.
Figure 8:
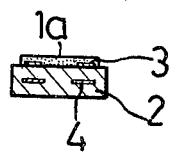
FIG. 8 is a sectional view taken along the line VIII—VIII of FIG. 7.
Figure 9:
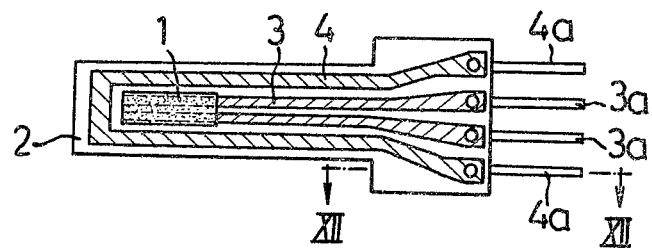
FIG. 9 is a plan view of a third embodiment of a detecting sensor according to the present invention.
Figure 10:
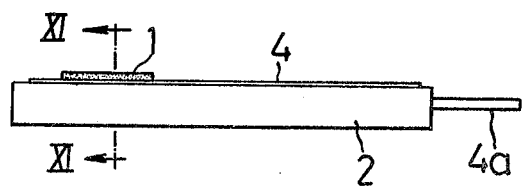
FIG. 10 is a side view of the third embodiment.
Figure 11:
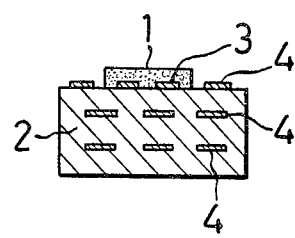
FIG. 11 is a sectional view taken along the line XI—XI of FIG. 10.
Figure 12:
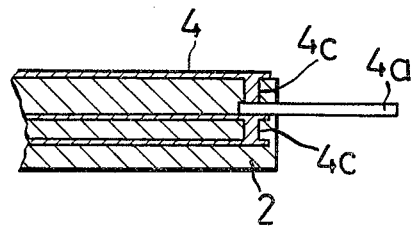
FIG. 12 is a sectional view taken along the line XII—XII of FIG. 9.

FIGS. 6 to 8 illustrate a second embodiment of a detecting sensor according to the present invention.

In the second embodiment, the electrodes 3 are completely covered by a heat resistant and electrically insulating thin protecting layer 1a such as an alumina layer in order to prevent the electrodes 3 from being exposed to exhaust gases.

According to the second embodiment, the short circuit can be prevented from occurring between the electrodes 3 due to the accumulation of conductive materials contained within exhaust gases, such as carbon.

FIGS. 9 to 12 illustrate a third embodiment of a gas detecting sensor according to the present invention.

On the surface of the base body 2, on which the electrodes 3 are formed, a film-shaped heater 4 is also formed.

Within the base body 2, two layered film-shaped heater 4 is formed. Three layers of the film-shaped heater 4 are connected to an electric power source through the lead wires 4a and lead members 4c in parallel. In this case, the electrodes 3 and the heater 4 formed on the surface of the base body 2 may be coated with the above described protecting cover.

According to the third embodiment, the heater 4 is composed of three layers which are connected to adjacent one in parallel so that the resistance of the heater can be made small.

Therefore, electric power required for maintaining the temperature of the heater 4 at a predetermined temperature can be supplied from the battery of which voltage is relatively low.

Furthermore, since the resistance of the heater can be made small, the area occupied by the heater can be decreased. Consequently, the size of the detecting sensor can be made small.

The sensing element according to the present invention, can be formed into a circular plate shape, a columnar shape or the like, of which thickness is relatively large.

These sensing elements are inferior to the film-shaped element in the responsive characteristic but are superior to the conventional element in the sensitivity to oxygen, since these sensing elements have the composition of 20 to 60 mol percent of cobalt monoxide, 20 to 60 mol percent of magnesium monoxide and 10 to 50 mol percent of nickel monoxide.

The protecting layer 1a can be also made of spinel, mullite, phorstellite, steatite or other heat resistant and electrically insulating material other than alumina. And the protecting layer 1a may be formed around the electrodes 3 by spraying method, plasma jetting method other than the screen printing method.

The senisng element may be made of salts such as nitrates of cobalt, magnesium and nickel other than oxides thereof.

And the sensing element may be formed on the base body by evaporating method, sputtering method or the like.

Furthermore, the sensing element may include inevitable impurities.

Having now fully described the invention, it will be apparent to one of ordinary skill in the art that many changes and modifications can be made thereto without departing from the spirit or scope of the invention as set forth herein.

What is claimed is:

1. A gas detecting sensor for detecting the partial pressure of oxygen gas contained within exhaust gases dishcarged from an engine, comprising:

a sensing element having such an electrical characteristic that the electrical resistance thereof changes in response to the partial pressure of oxygen gas;

said sensing element being formed of alloy ceramic material composed of 20 to 60 mol percent of cobalt monoxide, 20 to 60 mol percent of magnesium monoxide and 10 to 50 mol percent of nickel monoxide;

a base member formed of ceramic material for supporting said sensing element;

said base member being mounted to an exhaust passage of said engine so as to be exposed to said exhaust gases; and an electric current conducting means for supplying an electric current to said sensing element;

one end of said electric current conducting means bein electrically connected to said sensing element.

2. A gas detecting sensor according to claim 1, wherein:

said base member is formed of electrically insulating ceramic into a plate shape;

said sensing element is formed on the surface of said base member into a film shape; and said electric current conducting means is composed of a pair of electrodes and a pair of lead members, said electrodes are formed on the surface of said base member into a film shape so that one end of each electrode is connected to said sensing element while the other end thereof is connected to each of said lead members.

3. A gas detecting sensor according to claim 2, wherein:

said base member is made of alumina, spinel, mullite, phorstellite and steatite.

4. A gas detecting sensor according to claim 2, wherein:

said electrodes are made of platinum or platinum-rhodium alloy.

5. A gas detecting sensor according to claim 2, further comprising:

a heat resistant and electrically insulating layer which covers said electrodes.

6. A gas detecting sensor according to claim 2, further comprising:

a heating member for heating said sensing element and maintaining at a predetermined temperature.

7. A gas detecting sensor according to claim 6, wherein:

said heating member is provided within said base member.

8. A gas detecting sensor according to claim 6, wherein:

said heating member is provided on the surface of said base member.

9. A gas detecting sensor according to claim 7, wherein:

said heating member is composed of a plurality of layers which are arranged in the direction of thickness of said base member so as to be insulated from one another.

10. A gas detecting sensor according to claim 9, further comprising:

a layer of said heating member, which is formed on the surface of said base member so as to be connected to said plurality of layers in parallel and electrically connected to an electric power source.

11. A gas detecting sensor according to claim 6, wherein:

said heating member is formed of platinum, platinum-rhodium alloy, tungsten, or molybdenum-manganese alloy into a film shape.

12. A gas detecting sensor according to claim 6, wherein:

said base member is composed of an upper thin plate and a lower thin plate which are integrally combined with each other;

on the upper surface of said upper thin plate, one pair of said electrodes are printed so that said electrodes are formed at a predetermined interval and said sensing element is printed so as to cover one portion of said electrodes;

on the upper surface of said lower thin plate, said heating member is printed; and said upper thin plate on which said electrodes and said sensing element are formed, and said lower thin plate on which said heating member is formed, are combined by putting said upper thin plate on said lower thin plate and sintering together.

* * * * *